(12) United States Patent
Oomori et al.

(10) Patent No.: US 10,492,764 B2
(45) Date of Patent: Dec. 3, 2019

(54) ULTRASOUND DIAGNOSIS APPARATUS, MEDICAL IMAGE PROCESSING APPARATUS, AND MEDICAL IMAGE PROCESSING METHOD

(71) Applicant: Canon Medical Systems Corporation, Otawara-shi (JP)

(72) Inventors: Yoshihiro Oomori, Otawara Tochigi (JP); Go Tanaka, Utsunomiya Tochigi (JP); Eiji Goto, Utsunomiya Tochigi (JP); Osamu Nakajima, Otawara Tochigi (JP); Takayuki Gunji, Otawara Tochigi (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/803,897

(22) Filed: Nov. 6, 2017

(65) Prior Publication Data
US 2018/0125459 A1    May 10, 2018

(30) Foreign Application Priority Data

Nov. 10, 2016 (JP) .................................. 2016-219786
Sep. 15, 2017 (JP) .................................. 2017-178263

(51) Int. Cl.
*A61B 8/00* (2006.01)
*A61B 8/08* (2006.01)
*G06T 11/60* (2006.01)

(52) U.S. Cl.
CPC .......... *A61B 8/5292* (2013.01); *A61B 8/0825* (2013.01); *A61B 8/4245* (2013.01);
(Continued)

(58) Field of Classification Search
CPC ... A61B 8/5292; A61B 8/0825; A61B 8/4245; A61B 8/463; A61B 8/5207; G06T 11/60; G06T 2210/41
See application file for complete search history.

(56) References Cited

U.S. PATENT DOCUMENTS

| 2015/0146855 A1* | 5/2015 | Futamura | .............. | G06T 7/0012 |
| | | | | 378/63 |
| 2015/0150531 A1* | 6/2015 | Futamura | .............. | A61B 8/5261 |
| | | | | 378/37 |
| 2015/0178921 A1* | 6/2015 | Hashimoto | .............. | A61B 8/13 |
| | | | | 382/131 |

FOREIGN PATENT DOCUMENTS

| JP | 2008-264075 | 11/2008 |
| JP | 2012-135428 | 7/2012 |

* cited by examiner

*Primary Examiner* — Chong Wu
(74) *Attorney, Agent, or Firm* — Oblon, McClelland, Maier & Neustadt, L.L.P.

(57) ABSTRACT

According to one embodiment, an ultrasound diagnosis apparatus includes an acquisition unit, a selection unit, and a display control unit. The acquisition unit acquires a medical image accompanied by supplementary information indicating a site. The selection unit selects one of a plurality of instruction instruments each corresponding to a site. The display control unit displays the medical image, the instruction instrument, and an ultrasound image together on a display. Upon receipt of a change instruction to change either the instruction instrument or the medical image, the selection unit newly selects the medical image or the instruction instrument corresponding to the instruction instrument or the medical image after the change. The display control unit displays the instruction instrument or the medical image after the change, the medical image or the instruction instrument newly selected, and the ultrasound image together.

6 Claims, 8 Drawing Sheets

(52) U.S. Cl.
CPC .......... *A61B 8/4254* (2013.01); *A61B 8/4416* (2013.01); *A61B 8/46* (2013.01); *A61B 8/463* (2013.01); *A61B 8/465* (2013.01); *A61B 8/5207* (2013.01); *G06T 11/60* (2013.01); *G06T 2210/41* (2013.01)

ULTRASOUND DIAGNOSIS APPARATUS, MEDICAL IMAGE PROCESSING APPARATUS, AND MEDICAL IMAGE PROCESSING METHOD

CROSS-REFERENCE TO RELATED APPLICATION(S)

This application is based upon and claims the benefit of priority from Japanese Patent Application No. 2016-219786, filed Nov. 10, 2016; No. 2017-178263, filed Sep. 15, 2017 the entire contents of (all of) which are incorporated herein by reference.

FIELD

Embodiments described herein relate generally to an ultrasound diagnosis apparatus, a medical image processing apparatus, and a medical image processing method.

BACKGROUND

An ultrasound diagnosis apparatus sometimes has the function of displaying an ultrasound image together with a medical image acquired by another medical image diagnosis apparatus. Examples of the other medical image diagnosis apparatus include X-ray CT (computed tomography) systems, MRI (magnetic resonance imaging) equipment, X-ray diagnosis apparatuses, mammography apparatuses, and the like.

For example, in the ultrasound examination of the breasts, in some cases, an ultrasound diagnosis apparatus acquires and displays ultrasound images of the breasts while displaying a medical image (mammographic image) captured by a mammography apparatus as a reference image. An operator, such as a doctor or a technician, can perform the ultrasound examination for generating ultrasound images while referring to the mammographic image.

Generally, the mammographic image is generated by photographing the left and right breasts individually. Besides, it is difficult to distinguish between the left and right breasts by only viewing a mammogram depicted in the mammographic image. Therefore, in the ultrasound examination, the right site may be mistaken for the left site and vice versa between the mammographic image and the ultrasound image displayed.

Further, when switching between the left and right breasts to generate the ultrasound image thereof, the operator sometimes displays a mammographic image corresponding to the left or right breast after the change by entering an instruction for switching mammographic images to be displayed. This creates extra work in the operation procedure.

DETAILED DESCRIPTION

In general, according to one embodiment, an ultrasound diagnosis apparatus includes an acquisition unit, a selection unit, and a display control unit. The acquisition unit acquires a medical image accompanied by supplementary information indicating a site of a subject. The selection unit selects one of a plurality of instruction instruments each corresponding to a site. The display control unit displays the medical image, the instruction instrument, and an ultrasound image together on a display. Upon receipt of a change instruction to change either the instruction instrument or the medical image, the selection unit newly selects the medical image or the instruction instrument corresponding to the instruction instrument or the medical image after the change. The display control unit displays the instruction instrument or the medical image after the change, the medical image or the instruction instrument newly selected, and the ultrasound image together on the display.

Referring now to the drawings, a description is given of an ultrasound diagnosis apparatus, a medical image processing apparatus, and a medical image processing method according to embodiments.

First Embodiment

Figure 1:
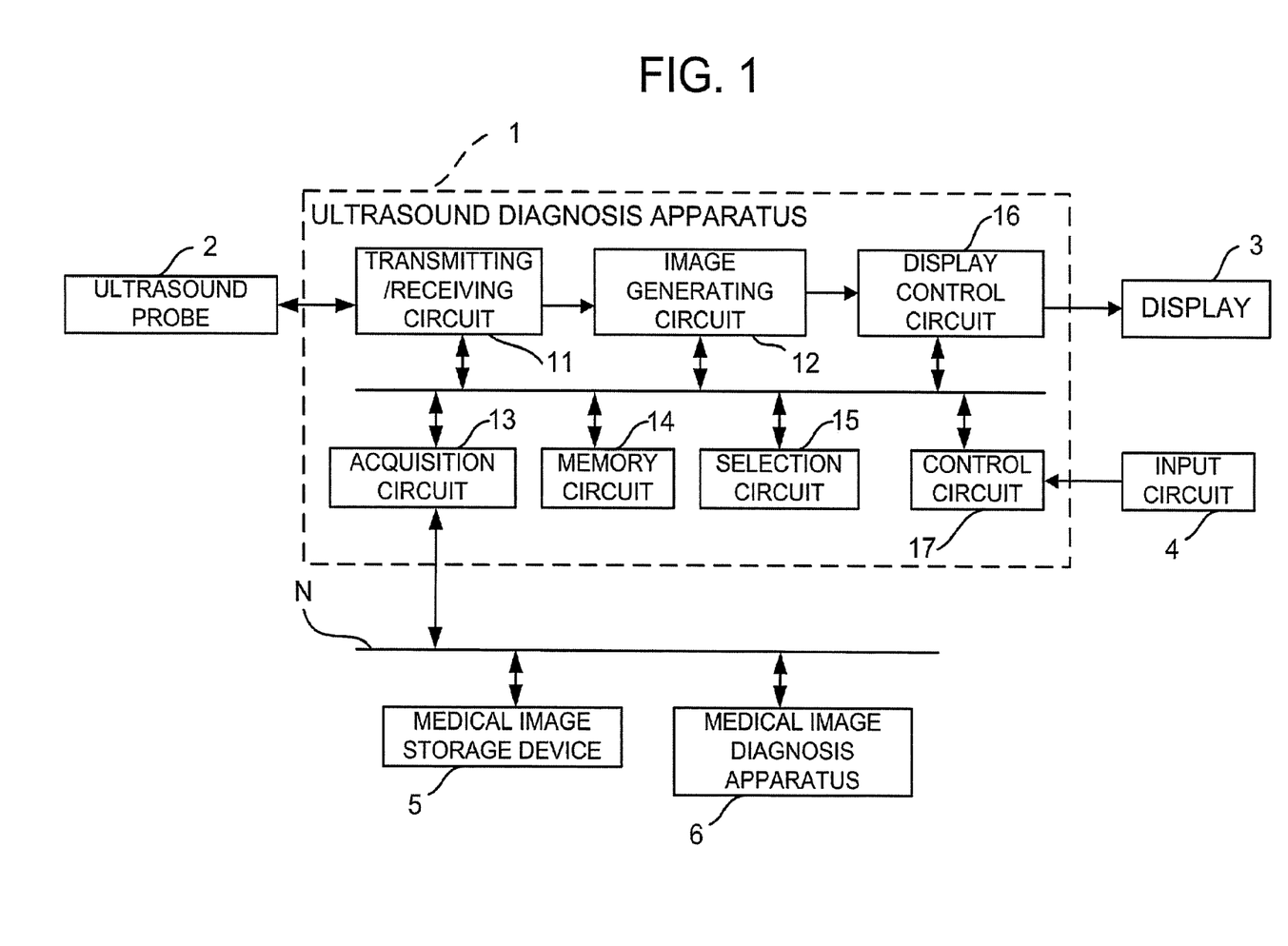
FIG. 1 is a block diagram illustrating a configuration of an ultrasound diagnosis apparatus according to a first embodiment.

FIG. 1 is a block diagram illustrating a configuration of an ultrasound diagnosis apparatus 1 according to a first embodiment. The ultrasound diagnosis apparatus 1 includes a transmitting/receiving circuit 11, an image generating circuit 12, an acquisition circuit 13, a memory circuit 14, a selection circuit 15, a display control circuit 16, and a control circuit 17. The ultrasound diagnosis apparatus 1 is communicably connected to an ultrasound probe 2, a display 3, and an input circuit 4. Further, the ultrasound diagnosis apparatus 1 is communicably connected to a medical image storage device 5 and a medical image diagnosis apparatus 6 via a network N.

[Basic Configuration]

The ultrasound probe 2 transmits ultrasound waves to a subject and receives reflected waves therefrom. The ultrasound probe 2 outputs an echo signal based on the reflected wave from the subject to the transmitting/receiving circuit 11.

The transmitting/receiving circuit 11 supplies an electric signal to the ultrasound probe 2 according to a control signal from the control circuit 17 to cause it to transmit ultrasound waves that have been beamformed to a predetermined focal point (i.e., subjected to transmission beamforming). Further, the transmitting/receiving circuit receives the echo signal from the ultrasound probe 2. The transmitting/receiving circuit 11 performs a delay process on the echo signal, thereby converting the analog echo signal into a received signal with phased addition. The transmitting/receiving circuit 11 outputs the received signal to the image generating circuit 12.

The image generating circuit 12 generates an ultrasound image based on the received signal from the transmitting/receiving circuit 11. For example, the image generating circuit 12 performs band-pass filtering on the received signal. Thereafter, the image generating circuit 12 detects the envelope of the output signal, and performs a compression process on the detected data by logarithmic conversion. The image generating circuit 12 converts the received signal subjected to the compression process (ultrasound raster data) into a coordinate system for display (scan conversion), thereby generating an ultrasound image. The image generating circuit 12 outputs the ultrasound image to the display control circuit 16.

The acquisition circuit 13 is a processor that acquires a medical image accompanied by supplementary information indicating a site of the subject. For example, the acquisition circuit 13 acquires a medical image of the subject from the medical image storage device 5 or the medical image diagnosis apparatus 6 based on an operation input provided by an operator. The acquisition circuit 13 outputs the medical image acquired to the memory circuit 14.

The medical image storage device 5 includes a database for storing medical images. Examples of medical images include X-ray CT images, MRI images, X-ray images, mammographic images, and the like. The medical image storage device 5 may store ultrasound images generated in the past. In the following, an example is described in which the medical image storage device 5 stores mammographic images. Examples of the medical image diagnosis apparatus 6 include an X-ray CT system, MRI equipment, an X-ray diagnosis apparatus, a mammography apparatus, and the like. In the following, the medical image diagnosis apparatus 6 is described as a mammography apparatus, for example. Generally, the medical image is accompanied by supplementary information indicating the site of the subject. For example, the supplementary information indicates the left/right of the site. The mammographic image is accompanied by supplementary information indicating the left and right of the breasts (whether it is the left breast or the right breast of the subject).

The memory circuit 14 stores the medical image received from the acquisition circuit 13. This medical image is displayed on the display 3 as a reference image during the ultrasound examination. Among medical images stored in the memory circuit 14, a medical image to be displayed first may be designated by a common process such as an operation input by the operator. The medical image designated is displayed as a reference image on the display 3.

In addition, the memory circuit 14 stores in advance a plurality of types of instruction instruments each corresponding to a site of the subject. A body mark may be cited as an example of the instruction instruments. For example, the memory circuit 14 stores in advance a plurality of types of body marks. The body mark is a schematic diagram schematically illustrating a site (chest, abdomen, breast, etc.) of the subject. Generally, with respect to the site that needs to be distinguished between the left and right (such as the breast), a body mark is stored in advance for each of the left and right sites.

The selection circuit 15 is a processor that selects a body mark corresponding to the site based on the supplementary information. For example, the selection circuit 15 reads the supplementary information of the medical image displayed as a reference image. The selection circuit 15 compares the site indicated by the supplementary information with the sites indicated by the body marks stored in the memory circuit 14. Thereby, the selection circuit 15 selects one of the body marks corresponding to the site of the reference image. The selection circuit 15 outputs the body mark selected to the display control circuit 16.

The display control circuit 16 is a processor that displays a medical image, a body mark, and an ultrasound image together on the display 3. The display 3 is formed of a display device such as a liquid crystal display (LCD) or an organic electro-luminescence (EL) display.

For example, the display control circuit 16 receives an operation input from the operator through the input circuit 4, reads out a medical image designated as a reference image from the memory circuit 14, and displays it on the display 3. Besides, the selection circuit 15 outputs a body mark selected for the medical image to the display control circuit 16. The display control circuit 16 displays the body mark on the display 3. In addition, the display control circuit 16 displays an ultrasound image received from the image generating circuit 12 on the display 3.

Figure 2:
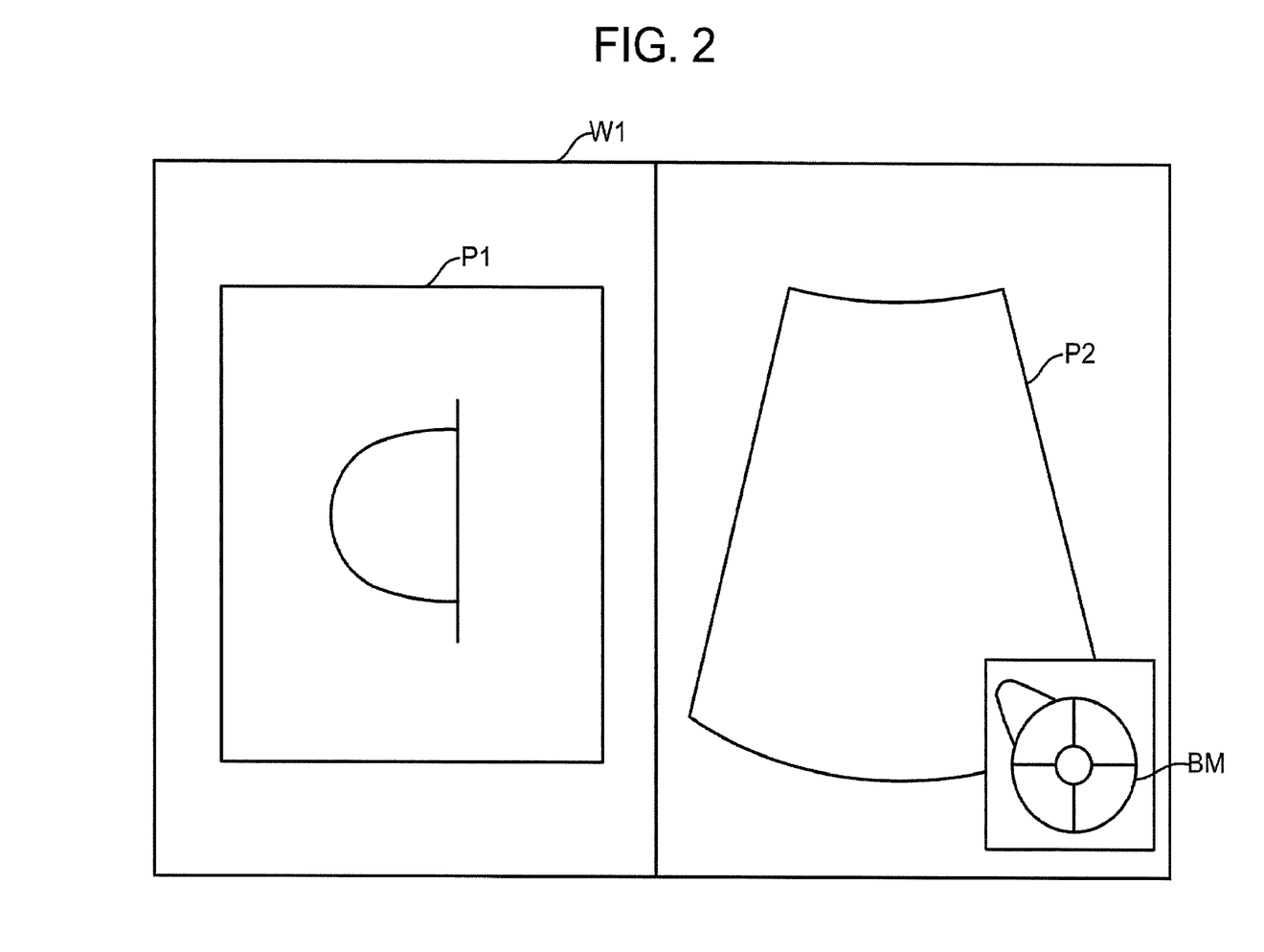
FIG. 2 is a schematic diagram illustrating a display example of a medical image, a body mark, and an ultrasound image.

FIG. 2 is a schematic diagram illustrating a display example of a medical image, a body mark, and an ultrasound image. In the example of FIG. 2, a mammographic image P1 is displayed on the left side of a display screen W1, an ultrasound image P2 is displayed on the right side, and a body mark BM is displayed on the lower right of the ultrasound image P2. The display layout on the display screen W1 may be set appropriately by presetting, operation input, or the like. The operator can perform an ultrasound examination while viewing the mammographic image P1, the ultrasound image P2, and the body mark BM displayed together. During the ultrasound examination, ultrasound images are sequentially generated at a predetermined frame rate. The display control circuit 16 receives the ultrasound images sequentially generated from the image generating circuit 12 and displays them on the display 3.

The input circuit 4 receives operation by the operator such as a doctor, a technician, or the like, and outputs a signal corresponding to the content of the operation to the control circuit 17. The input circuit 4 includes, for example, a trackball, a switch button, a mouse, a keyboard, a touch command screen (TCS), a sensitivity time control (STC) slide volume, and the like.

The control circuit 17 is a processor that controls the operation of each part of the ultrasound diagnosis apparatus 1. The control circuit 17 stores a medical image processing program for controlling each part of the ultrasound diagnosis apparatus 1 and executes it (details are described later).

[Configuration for Changing Medical Image in Conjunction with Body Mark Change Instruction]

Described below is a configuration of the ultrasound diagnosis apparatus 1 for changing the medical image in conjunction with an instruction to change the body mark.

During the ultrasound examination, the operator may input a change instruction to change the body mark using the input circuit 4. Upon receipt of the change instruction, the selection circuit 15 newly selects a medical image corresponding to a body mark after the change indicated by the change instruction. For example, when the medical image is a mammographic image and the supplementary information indicates the left/right of the site, the change instruction instructs to change the body mark of the left breast to the body mark of the right breast and vice versa. The selection circuit 15 compares the change instruction with the supplementary information of each medical image (mammographic image) stored in the memory circuit 14, thereby newly selecting a mammographic image accompanied by supplementary information indicating the site changed according to the change instruction (right breast or left breast) from the memory circuit 14. The selection circuit 15 outputs the mammographic image newly selected to the display control circuit 16. The selection circuit 15 may select a medical image of the site after the change from the medical image storage device 5 or the medical image diagnosis apparatus 6.

The display control circuit 16 displays the body mark changed and the mammographic image newly selected on the display 3 together with an ultrasound image. That is, during the ultrasound examination, the reference image (e.g., mammographic image) is changed and displayed in conjunction with the change of the body mark. In this manner, a reference image corresponding to the site changed according to an instruction to change the body mark is automatically displayed. Thus, it is possible to prevent mistakes about the site of the reference image as well as to improve the operability.

Figure 3:
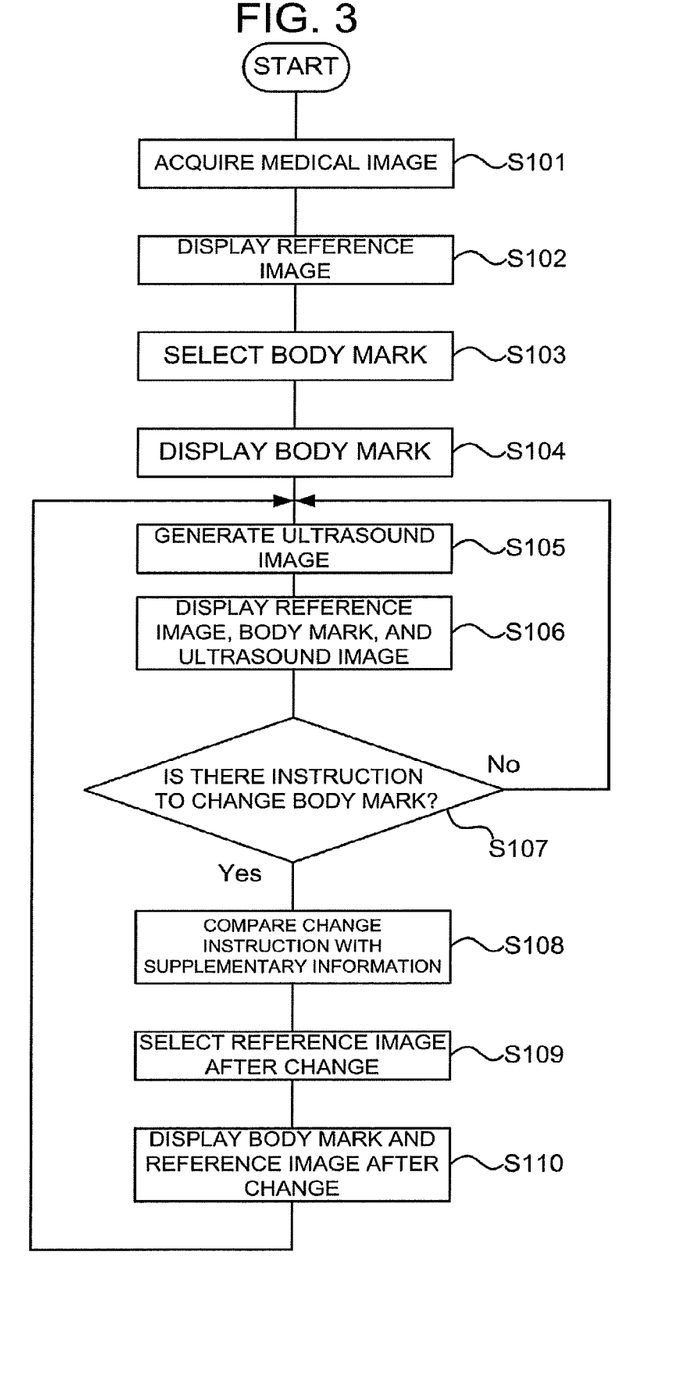
FIG. 3 is a flowchart illustrating the operation of the ultrasound diagnosis apparatus of the first embodiment to change the medical image in conjunction with the change of the body mark.

FIG. 3 is a flowchart illustrating the operation of the ultrasound diagnosis apparatus 1 of the first embodiment to change the medical image in conjunction with the change of the body mark. For example, the control circuit 17 stores a program that implements the following medical image processing method and executes it.

Step S101: The acquisition circuit 13 reads out a medical image of the subject from the medical image storage device 5 or the medical image diagnosis apparatus 6 based on an operation input provided by the operator. The acquisition circuit 13 outputs the medical image to the memory circuit 14.

Step S102: The display control circuit 16 receives an operation input from the operator through the input circuit 4, reads out a medical image designated as a reference image from the memory circuit 14, and displays it on the display 3.

Step S103: The selection circuit 15 reads the supplementary information of the medical image displayed as a reference image. The selection circuit 15 compares the site indicated by the supplementary information with the sites indicated by a plurality of types of body marks stored in the memory circuit 14. Thereby, the selection circuit 15 selects one of the body marks corresponding to the site of the reference image.

Step S104: The selection circuit 15 outputs the body mark selected to the display control circuit 16. The display control circuit 16 displays the body mark on the display 3.

Step S105: The operator performs an ultrasound examination using the ultrasound probe 2 and the input circuit 4. At this time, the transmitting/receiving circuit 11 supplies an electric signal to the ultrasound probe 2 according to a control signal from the control circuit 17 to cause it to transmit ultrasound waves that have been beamformed to a predetermined focal point. The ultrasound probe 2 transmits ultrasound waves to the subject and receives reflected waves from the subject. The transmitting/receiving circuit 11 receives an echo signal from the ultrasound probe 2. The image generating circuit 12 generates an ultrasound image based on the received signal from the transmitting/receiving circuit 11. The image generating circuit 12 outputs the ultrasound image to the display control circuit 16.

Step S106: The display control circuit 16 displays the medical image, the body mark, and the ultrasound image together on the display 3.

Step S107, Step S108: Upon receipt of an instruction to change the body mark (Yes in step S107), the selection circuit 15 newly checks a medical image corresponding to the body mark after the change. For example, when the medical image is a mammographic image and the supplementary information indicates the left/right of the site, the selection circuit 15 compares the change instruction with the supplementary information of medical images stored in the memory circuit 14. When there is no instruction to change the body mark (No in step S107), steps S105 and S106 are repeated.

Step S109: The selection circuit 15 newly selects a mammographic image (medical image) accompanied by supplementary information indicating the site after the change (right breast or left breast) from the memory circuit 14. The selection circuit 15 outputs the mammographic image newly selected to the display control circuit 16.

Step S110: The display control circuit 16 displays the body mark changed and the mammographic image newly selected on the display 3 together with the ultrasound image.

As described above, according to the first embodiment, the ultrasound diagnosis apparatus 1 automatically displays a reference image corresponding to the site changed according to an instruction to change the body mark. Thus, it is possible to prevent mistakes about the site of the reference image as well as to improve the operability.

[Configuration for Changing Body Mark in Conjunction with Medical Image Change Instruction]

Described below is a configuration of the ultrasound diagnosis apparatus 1 for changing the body mark in conjunction with an instruction to change the medical image.

During the ultrasound examination, the operator may input a change instruction to change the medical image using the input circuit 4. Upon receipt of the change instruction, the selection circuit 15 newly selects a body mark corresponding to a medical image after the change indicated by the change instruction. For example, when the medical image is a mammographic image and the supplementary information indicates the left/right of the site, the change instruction instructs to change the mammographic image of the left breast to the mammographic image of the right breast and vice versa. The selection circuit 15 compares the site indicated by the supplementary information of the medical image indicated by the change instruction with the site indicated by each body mark stored in the memory circuit 14, thereby newly selecting a body mark corresponding to the site of the medical image changed according to the change instruction (right breast or left breast) from the memory circuit 14. The selection circuit 15 outputs the body mark newly selected to the display control circuit 16.

The display control circuit 16 displays the mammographic image changed and the body mark newly selected on the display 3 together with an ultrasound image. That is, during the ultrasound examination, the body mark is changed and displayed in conjunction with the change of the reference image (e.g., mammographic image). In this manner, a body mark corresponding to the site changed according to an instruction to change the reference image is automatically displayed. Thus, it is possible to prevent mistakes about the site of the body mark as well as to improve the operability.

Figure 4:
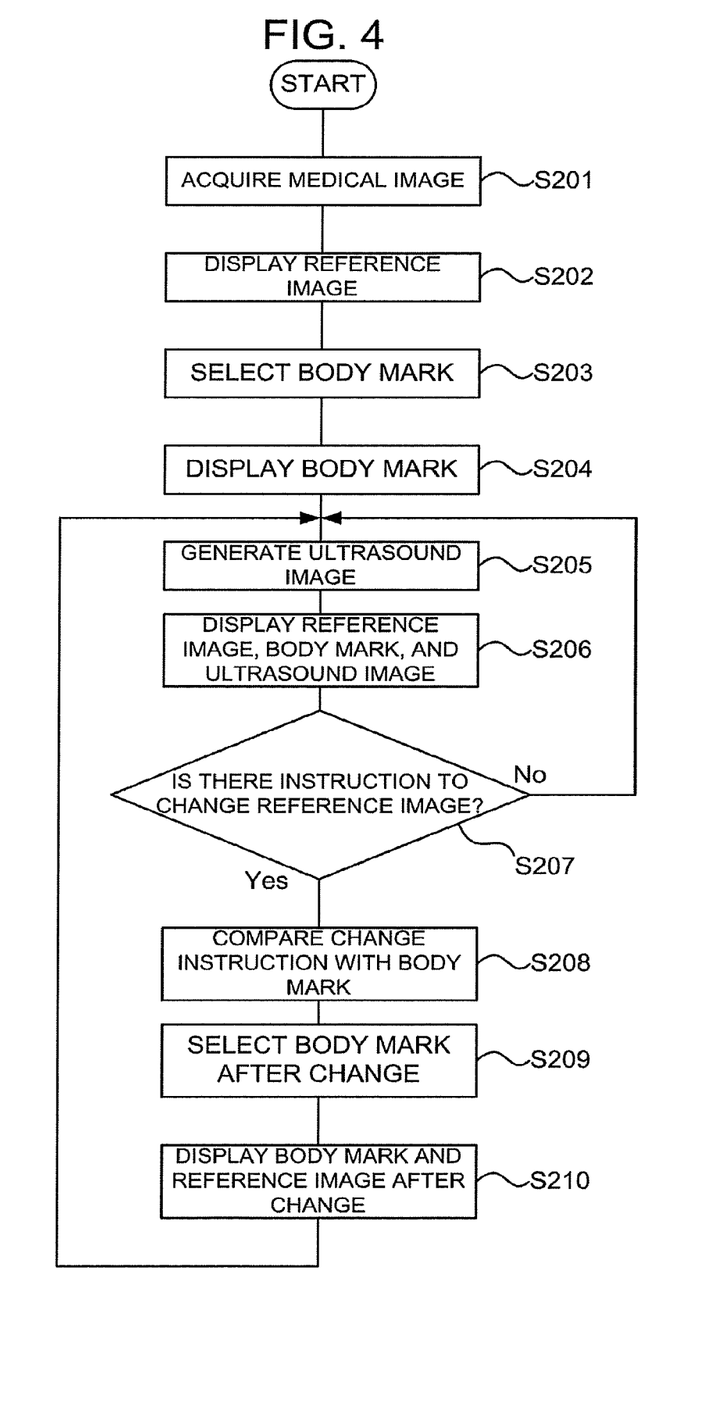
FIG. 4 is a flowchart illustrating the operation of the ultrasound diagnosis apparatus of the first embodiment to change the body mark in conjunction with the change of the medical image.

FIG. 4 is a flowchart illustrating an operation of the ultrasound diagnosis apparatus 1 of the first embodiment to change the body mark in conjunction with the change of the medical image. For example, the control circuit 17 stores a program that implements the following medical image processing method and executes it.

Step S201: The acquisition circuit 13 reads out a medical image of the subject from the medical image storage device 5 or the medical image diagnosis apparatus 6 based on an operation input provided by the operator. The acquisition circuit 13 outputs the medical image to the memory circuit 14.

Step S202: The display control circuit 16 receives an operation input from the operator through the input circuit 4, reads out a medical image designated as a reference image from the memory circuit 14, and displays it on the display 3.

Step S203: The selection circuit 15 reads the supplementary information of the medical image displayed as a reference image. The selection circuit 15 compares the site indicated by the supplementary information with the sites indicated by a plurality of types of body marks stored in the memory circuit 14. Thereby, the selection circuit 15 selects one of the body marks corresponding to the site of the reference image.

Step S204: The selection circuit 15 outputs the body mark selected to the display control circuit 16. The display control circuit 16 displays the body mark on the display 3.

Step S205: The operator performs an ultrasound examination using the ultrasound probe 2 and the input circuit 4. At this time, the transmitting/receiving circuit 11 supplies an electric signal to the ultrasound probe 2 according to a control signal from the control circuit 17 to cause it to transmit ultrasound waves that have been beamformed to a predetermined focal point. The ultrasound probe 2 transmits ultrasound waves to the subject and receives reflected waves from the subject. The transmitting/receiving circuit 11 receives an echo signal from the ultrasound probe 2. The image generating circuit 12 generates an ultrasound image based on the received signal from the transmitting/receiving circuit 11. The image generating circuit 12 outputs the ultrasound image to the display control circuit 16.

Step S206: The display control circuit 16 displays the medical image (reference image), the body mark, and the ultrasound image together on the display 3.

Step S207, Step S208: Upon receipt of an instruction to change the reference image (Yes in step S207), the selection circuit 15 newly selects a body mark corresponding to the site of the reference image after the change. For example, when the medical image is a mammographic image and the supplementary information indicates the left/right of the site, the selection circuit 15 compares the site indicated by the supplementary information of the reference image after the change with the site indicated by each body mark stored in the memory circuit 14. When there is no instruction to change the reference image (No in step S207), steps S205 and S206 are repeated.

Step S209: The selection circuit 15 newly selects a body mark indicating the site of the reference image after the change from the memory circuit 14. The selection circuit 15 outputs the body mark newly selected to the display control circuit 16.

Step S210: The display control circuit 16 displays the reference image changed and the body mark newly selected on the display 3 together with the ultrasound image.

As described above, according to the first embodiment, the ultrasound diagnosis apparatus 1 automatically displays a body mark corresponding to the site changed according to an instruction to change the reference image. Thus, it is possible to prevent mistakes about the site of the body mark as well as to improve the operability.

Modification of First Embodiment

Figure 5:
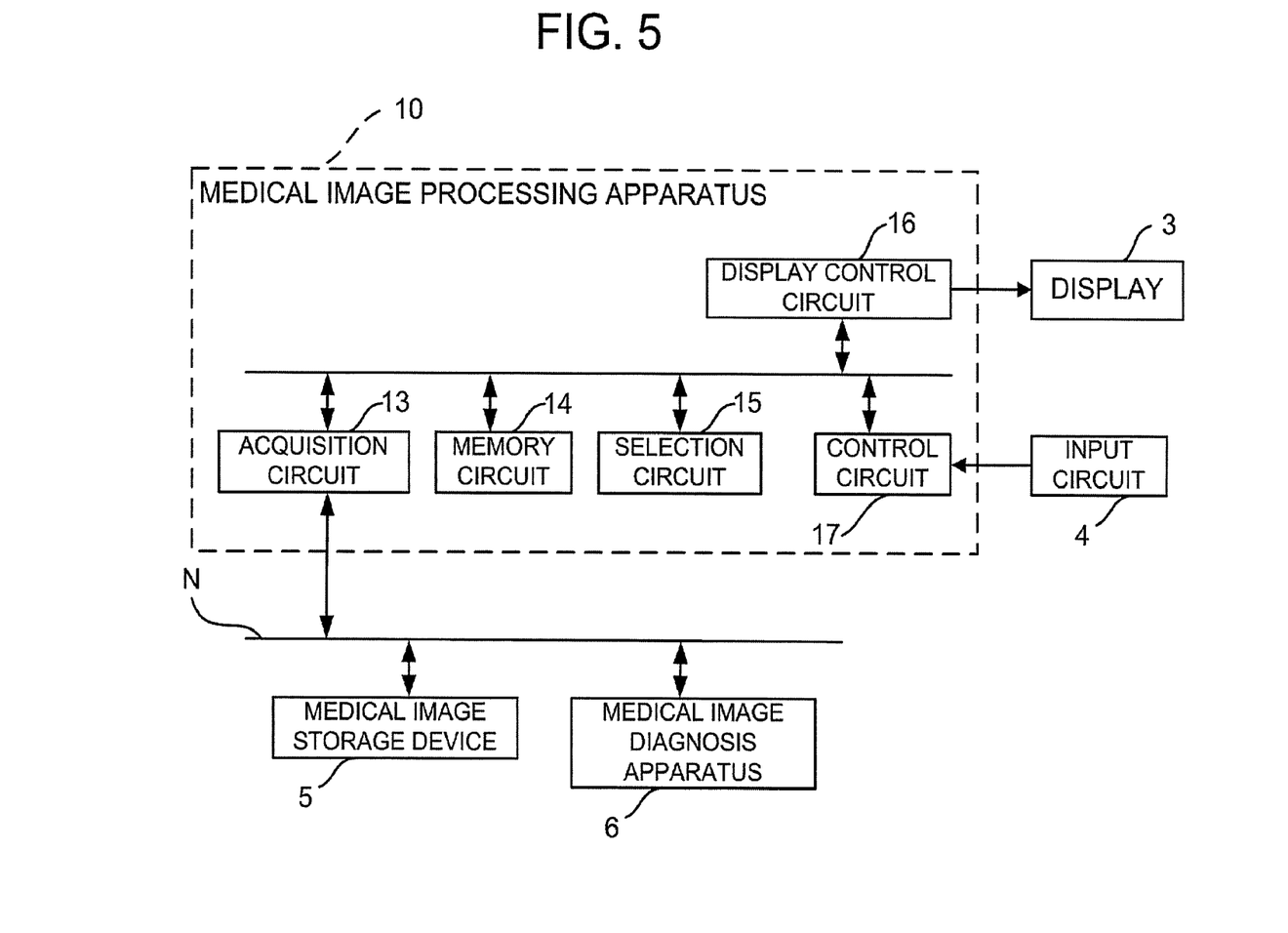
FIG. 5 is a block diagram illustrating a configuration of a medical image processing apparatus according to a modification.

A modification of the first embodiment is described. This modification relates to a medical image processing apparatus. FIG. 5 is a block diagram illustrating a configuration of a medical image processing apparatus 10 of the modification. In the following, differences from the first embodiment are mainly described. The same description as has already been provided in the first embodiment may not be repeated.

The acquisition circuit 13 acquires an ultrasound image and a medical image as a reference image from the medical image storage device 5 based on an operation input provided by the operator. The acquisition circuit 13 stores the ultrasound image and the medical image as a reference image in the memory circuit 14. In the medical image processing apparatus 10 having the acquisition circuit 13, for example, an ultrasound image generated in a past ultrasound examination may sometimes be displayed together with a body mark and a reference image for comparison. In this case, the ultrasound image may be displayed as a moving image. While the moving image is being displayed, if the ultrasound image displayed and the site of the body mark (e.g., left breast or right breast) are changed, a reference image of the corresponding site may be newly displayed in conjunction with the change.

For example, while the moving image is being displayed, the control circuit 17 refers to the body mark of a frame (ultrasound image) displayed at a predetermined frame rate. Thereby, the control circuit 17 specifies the site of the frame displayed. In addition, the control circuit 17 compares the site most recently specified with the site one frame previous to it, and determines whether the site has been changed. Having determined that the site has been changed, the control circuit 17 outputs an instruction to change the reference image to the selection circuit 15.

According to the change instruction from the control circuit 17, the selection circuit 15 compares the site indicated by the change instruction with the supplementary information of each medical image stored in the memory circuit 14, thereby newly selecting a reference image (mammographic image) accompanied by supplementary information indicating the site changed according to the change instruction (right breast or left breast) from the memory circuit 14.

Further, in the medical image processing apparatus 10, a medical image that contains a plurality of sites may sometimes be displayed as a reference image. Examples of the medical image that contains a plurality of sites include a mammographic image obtained by combining a left breast image and a right breast image together (hereinafter referred to as "left-right combined mammographic image"). Generally, the left-right combined mammographic image is generated by combining mammographic images of the left breast and the right breast captured separately. The supplementary information attached to the individual mammographic images before being combined is attached in association with a range in the left-right combined mammographic image. In this case, when an enlarged view of the left breast side or the right breast side of the left-right combined mammographic image is displayed, the body mark may be changed correspondingly to the site in the display range.

For example, while a left-right combined mammographic image is being displayed as a reference image, the operator may operate the input circuit 4 to provide an operation input to display an enlarged view of the left breast side or the right breast side of the left-right combined mammographic image. When such an operation input is provided, the display control circuit 16 specifies the display range of the left-right combined mammographic image from coordinates or the like based on the operation input, and displays an enlarged view of the display range. The display control circuit 16 outputs the display range to the selection circuit 15.

The selection circuit 15 refers to the supplementary information associated with the enlarged display range. Thereby, the selection circuit 15 specifies the site of the display range. The selection circuit 15 selects a body mark indicating the site specified. The selection circuit 15 reads out the body mark selected from the memory circuit 14 and outputs it to the display control circuit 16. The display control circuit 16 displays the body mark on the display 3.

Besides, in conjunction with the change of the body mark, an enlarged view of a range of the left-right combined mammographic image may be displayed. For example, the operator may operate the input circuit 4 to provide an operation input to change the body mark. The selection circuit 15 compares the site indicated by the body mark changed according to the operation input with the site indicated by the supplementary information of the left-right combined mammographic image, and selects the display range corresponding to the body mark. The selection circuit 15 outputs the body mark and the display range to the display control circuit 16. The display control circuit 16 displays the body mark and enlarged view of the display range.

With the medical image processing apparatus of the modification, it is possible to prevent mistakes about the site of the reference image as well as to improve the operability.

Second Embodiment

Figure 6:
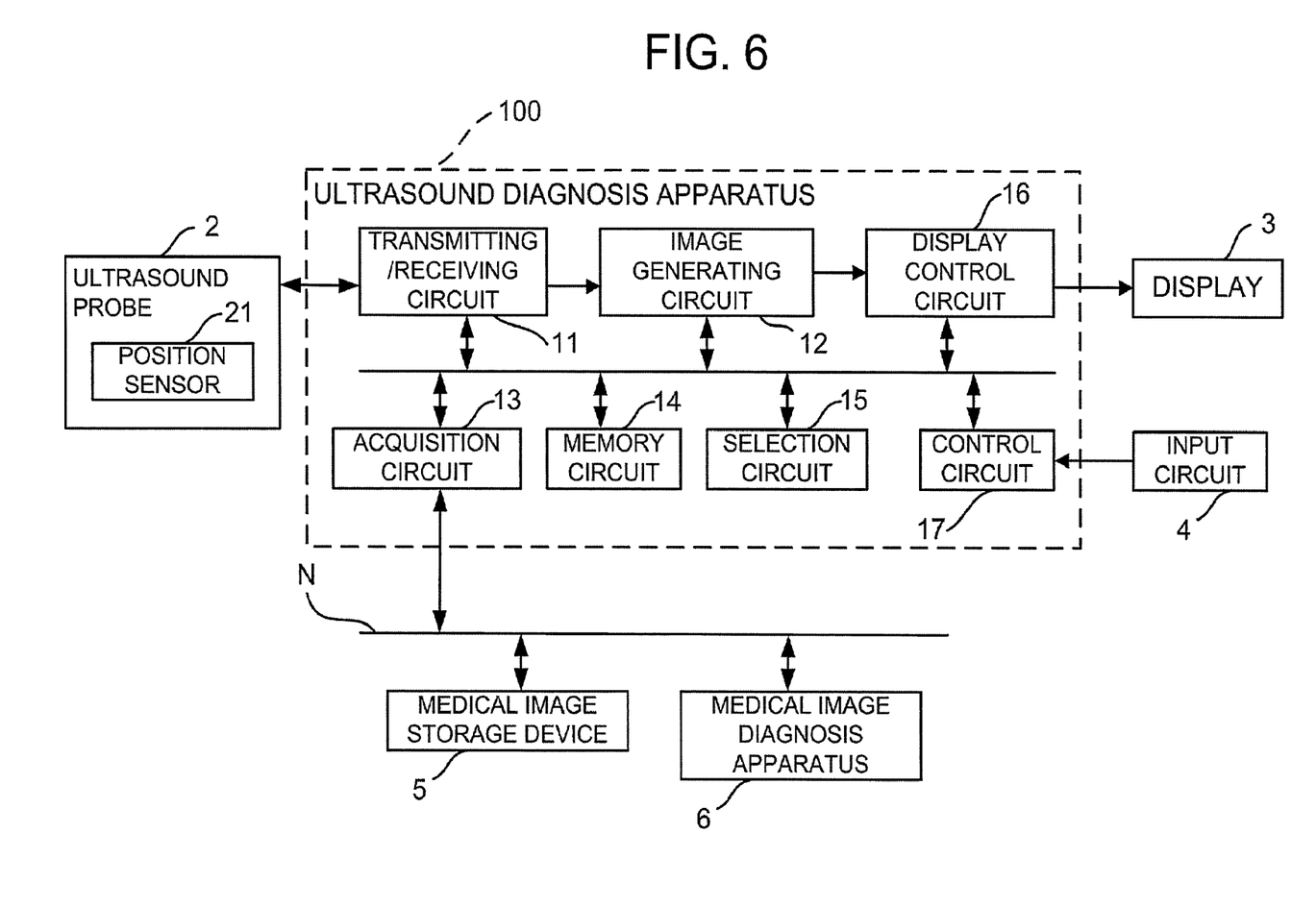
FIG. 6 is a block diagram illustrating a configuration of an ultrasound diagnosis apparatus according to a second embodiment.

FIG. 6 is a block diagram illustrating a configuration of an ultrasound diagnosis apparatus 100 according to a second embodiment. The ultrasound diagnosis apparatus 100 of the second embodiment changes the reference image and the body mark displayed according to the position of the ultrasound probe 2. In the following, differences from the first embodiment are mainly described. The same description as has already been provided in the first embodiment may not be repeated.

The ultrasound probe 2 includes a position sensor 21. The position sensor 21 sequentially detects the position of the ultrasound probe 2 that is transmitting/receiving ultrasound waves. A general magnetic sensor or optical sensor may be used for the hardware configuration of the position sensor 21. The position sensor 21 outputs position information detected to the ultrasound diagnosis apparatus 100. For example, the control circuit 17 sequentially specifies the position of the ultrasound probe 2 based on the position information.

The selection circuit 15 sequentially selects a medical image (reference image) and a body mark corresponding to the position of the ultrasound probe 2 based on position information obtained by the position sensor 21 and the supplementary information of the medical image. For example, based on the position information, the selection circuit 15 sequentially determines whether the ultrasound probe 2 is located in the left breast or in the right breast, i.e., the left/right of the site (breast) corresponding to the position of the ultrasound probe 2. At this time, the boundary between the left and right of the site may be set as appropriate. Examples of the boundary include a perpendicular bisector of a line segment connecting the nipples of the left breast and the right breast. The reference position of the nipple or the like may be set as appropriate. In this example, the selection circuit 15 determines whether the ultrasound probe 2 is located on the left side or the right side of the boundary, thereby sequentially determining the left/right of the site corresponding to the position of the ultrasound probe 2.

The selection circuit 15 compares the site with the supplementary information of each medical image acquired to select a medical image corresponding to the site. Thereby, a medical image corresponding to the position of the ultrasound probe 2 is selected as a reference image. The selection circuit 15 outputs the medical image selected to the display control circuit 16.

In addition, the selection circuit 15 compares the site with the site indicated by each body mark stored to select a body mark corresponding to the site. Thereby, a body mark corresponding to the position of the ultrasound probe 2 is selected. The selection circuit 15 outputs the body mark selected to the display control circuit 16.

The display control circuit 16 sequentially displays the medical image (reference image) and the body mark received form the selection circuit 15 on the display 3 together with an ultrasound image. Thereby, the reference image and the body mark are displayed according to the position of the ultrasound probe 2. Thus, it is possible to prevent mistakes about the site of the body mark and the reference image as well as to improve the operability.

Figure 7:
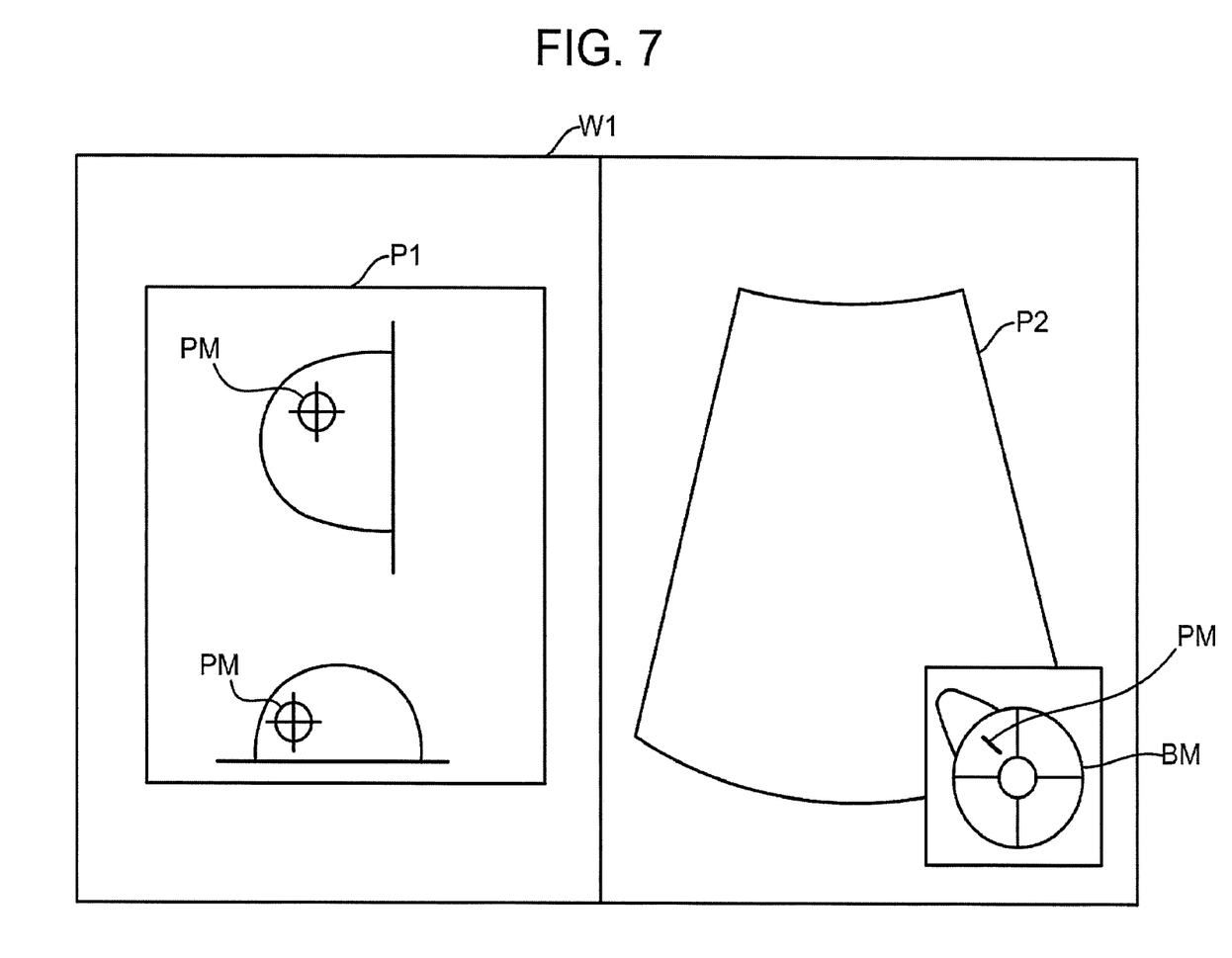
FIG. 7 is a schematic diagram illustrating a display example of a medical image, a body mark, and an ultrasound image.

FIG. 7 is a schematic diagram illustrating a display example of a medical image, a body mark, and an ultrasound image. In the example of FIG. 7, the mammographic image P1 is displayed on the left side of the display screen W1, the ultrasound image P2 is displayed on the right side, and the body mark BM is displayed on the lower right of the ultrasound image P2. The operator can perform an ultrasound examination while viewing the mammographic image P1, the ultrasound image P2, and the body mark BM displayed together according to the position of the ultrasound probe 2. The display control circuit 16 may display a probe mark PM indicating the position of the ultrasound probe 2 in a superimposed manner on the mammographic image P1 and the body mark BM based on the position of the ultrasound probe 2 detected.

Figure 8:
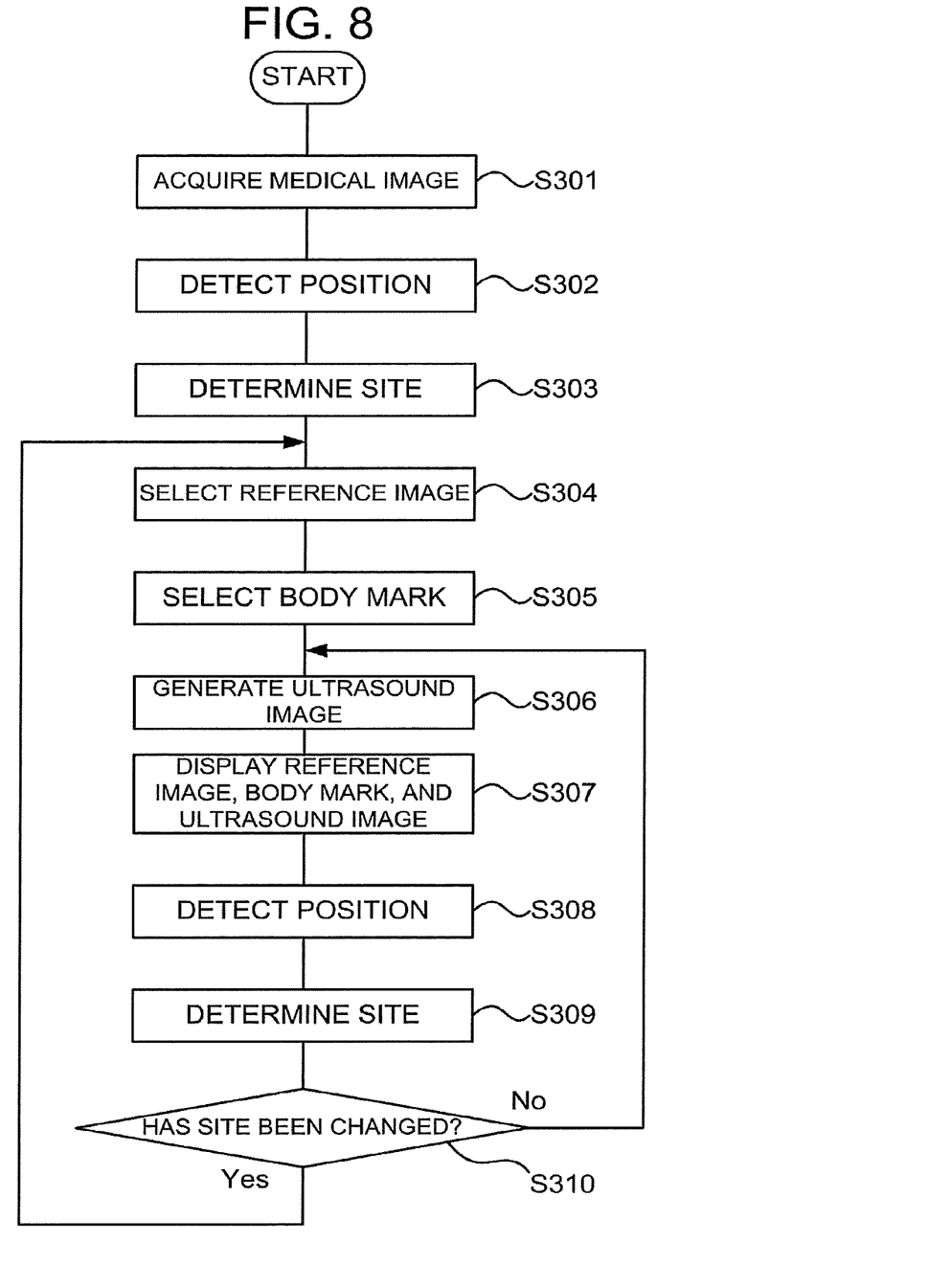
FIG. 8 is a flowchart illustrating the operation of the ultrasound diagnosis apparatus of the second embodiment.

FIG. 8 is a flowchart illustrating the operation of the ultrasound diagnosis apparatus 100 of the second embodiment. For example, the control circuit 17 stores a program that implements the following medical image processing method and executes it.

Step S301: The acquisition circuit 13 reads out a medical image of the subject from the medical image storage device 5 or the medical image diagnosis apparatus 6 based on an operation input provided by the operator. The acquisition circuit 13 outputs the medical image to the memory circuit 14.

Step S302: The position sensor 21 sequentially detects the position of the ultrasound probe 2. The position sensor 21 outputs position information detected to the ultrasound diagnosis apparatus 100.

Step S303: The selection circuit 15 determines the left/right of the site corresponding to the position of the ultrasound probe 2 based on the position information.

Step S304: The selection circuit 15 compares the site with the site indicated by the supplementary information of each medical image acquired to select a medical image corresponding to the site. Thereby, a medical image corresponding to the position of the ultrasound probe 2 is selected as a reference image. The selection circuit 15 outputs the medical image selected to the display control circuit 16.

Step S305: The selection circuit 15 compares the site with the site indicated by each body mark stored to select a body mark corresponding to the site. Thereby, a body mark corresponding to the position of the ultrasound probe 2 is selected. The selection circuit 15 outputs the body mark selected to the display control circuit 16.

Step S306: The operator performs an ultrasound examination using the ultrasound probe 2 and the input circuit 4. At this time, the transmitting/receiving circuit 11 supplies an electric signal to the ultrasound probe 2 according to a control signal from the control circuit 17 to cause it to transmit ultrasound waves that have been beamformed to a predetermined focal point. The ultrasound probe 2 transmits ultrasound waves to the subject and receives reflected waves from the subject. The transmitting/receiving circuit 11 receives an echo signal from the ultrasound probe 2. The image generating circuit 12 generates an ultrasound image based on the received signal from the transmitting/receiving circuit 11. The image generating circuit 12 outputs the ultrasound image to the display control circuit 16.

Step S307: The display control circuit 16 displays the medical image (reference image), the body mark, and the ultrasound image together on the display 3.

Step S308: The position sensor 21 newly detects the position of the ultrasound probe 2. The position sensor 21 outputs position information detected to the ultrasound diagnosis apparatus 100.

Step S309: The selection circuit 15 newly determines the left/right of the site corresponding to the position of the ultrasound probe 2 based on the position information.

Step S310: The selection circuit 15 compares the site newly determined with the site one frame previous to it, thereby determining whether the site has been changed. When the site has been changed (Yes in step S310), the process returns to step S304. When the site has not been changed (No in step S310), the process returns to step S306.

As described above, according to the second embodiment, the ultrasound diagnosis apparatus 100 obtains the site according to the position of the ultrasound probe, and sequentially selects a reference image and a body mark corresponding to the site. Thus, it is possible to prevent mistakes about the reference image and the body mark as well as to improve the operability.

While an ultrasound examination, in which an ultrasound image is generated by using a mammographic image as a reference image, has been described as an example, the above embodiments may be applied to other examinations. Examples of the other examinations include ultrasound examination in which the target site is the thyroid gland and an ultrasound image is generated by using a CT image illustrating the thyroid gland as a reference image, and ultrasound examination in which the target site is the prostate and an ultrasound image is generated by using an MR image illustrating the prostate as a reference image.

The term "processor" as used herein refers to a circuit such as, for example, a central processing unit (CPU), a graphics processing unit (GPU), an application specific integrated circuit (ASIC), a programmable logic device including a simple programmable logic device (SPLD) and a complex programmable logic device (CPLD), a field programmable gate array (FPGA), or the like. The processor reads programs out of a memory circuit and executes them to thereby realize the functions. The programs need not necessarily be stored in a memory circuit, but may be directly incorporated in the circuit of the processor. In this case, the processor realizes the functions by reading and executing the programs incorporated in the circuit. Each processor of the embodiment need not necessarily be configured as a single circuit. A plurality of independent circuits may be combined to form a single processor for implementing the functions. Besides, a plurality of constituent elements in each embodiment may be integrated into one processor to realize the functions.

With the ultrasound diagnosis apparatus, the medical image processing apparatus, and the medical image processing method of at least one embodiment described above, it is possible to prevent mistakes about the site of the subject indicated by the body mark and the reference image as well as to improve the operability.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without desiteing from the spirit of the inventions. The accompanying claims and their equivalents are intended to cover such forms or modifications as would fall within the scope and spirit of the inventions.

What is claimed is:

1. An ultrasound diagnosis apparatus configured to generate an ultrasound image, comprising:
   processing circuitry configured to
   acquire a medical image that is different from the ultrasound image and accompanied by supplementary information indicating a site of a subject;
   select a body mark corresponding to the site from a plurality of body marks; and
   display the medical image, the selected body mark, and the ultrasound image together on a display, wherein
   upon receipt of a change instruction to change one of the body mark and the medical image, the processing circuitry is further configured to newly select another of the medical image and the body mark to correspond to the one of the body mark and the medical image that has been changed, and
   the processing circuitry is further configured to display the one of the body mark and the medical image that has been changed, the another of the medical image and the body mark newly selected, and the ultrasound image together on the display.

2. The ultrasound diagnosis apparatus of claim 1, wherein the supplementary information indicates a left or a right of the site, and
   the processing circuitry is further configured to select the body mark corresponding to the left or the right of the site, and, upon receipt of the change instruction, newly select the other of the medical image and the body mark to correspond to the left or the right of the site that has been changed.

3. A medical image processing apparatus, comprising:
   processing circuitry configured to
   acquire an ultrasound image and a medical image that is different from the ultrasound image and accompanied by supplementary information indicating a site of a subject;
   select a body mark corresponding to the site from a plurality of body marks; and
   display the medical image, the body mark, and the ultrasound image together on a display, wherein
   upon receipt of a change instruction to change one of the body mark and the medical image, the processing circuitry is further configured to newly select another of the medical image and the body mark to correspond to the one of the body mark and the medical image that has been changed, and the processing circuitry is further configured to display the one of the body mark and the medical image that has been changed, the another of the medical image and the body mark newly selected, and the ultrasound image together on the display.

4. The medical image processing apparatus of claim 3, wherein the medical image contains a plurality of sites, the supplementary information is associated with a plurality of display ranges in the medical image, and the processing circuitry is further configured to specify a site in a particular display range of the medical image based on the plurality of display ranges and the supplementary information, and select the body mark corresponding to the specified site in the particular display range, and, upon receipt of a change instruction to change the particular display range, newly select the body mark corresponding to the particular display range that has been changed.

5. The medical image processing apparatus of claim 3, wherein the medical image contains a plurality of sites, the supplementary information is associated with a plurality of display ranges in the medical image, and the processing circuitry is further configured to specify a site in a particular display range of the medical image based on the plurality of display ranges and the supplementary information, and select the body mark corresponding to the specified site in the particular display range, and, upon receipt of the change instruction, newly select a new display range corresponding to the body mark that has been changed.

6. A medical image processing method, comprising:

acquiring an ultrasound image and a medical image that is different from the ultrasound image and accompanied by supplementary information indicating a site of a subject;

selecting a body mark corresponding to the site from a plurality of body marks;

displaying the medical image, the body mark, and the ultrasound image together on a display, newly selecting, upon receipt of a change instruction to change one of the body mark and the medical image, another of the medical image and the body mark to correspond to the one of the body mark and the medical image that has been changed, and displaying the one of the body mark and the medical image that has been changed, the another of the medical image and the body mark newly selected, and the ultrasound image together on the display.

* * * * *